(12) United States Patent
Zardi et al.

(10) Patent No.: US 9,765,041 B2
(45) Date of Patent: *Sep. 19, 2017

(54) INTEGRATED PROCESS FOR UREA AND MELAMINE PRODUCTION

(71) Applicant: Casale SA, Lugano (CH)

(72) Inventors: Federico Zardi, Breganzona (CH); Paolo Sticchi, Massagno (CH); Paolo Brunengo, Woking (GB)

(73) Assignee: Casale SA (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/070,779

(22) Filed: Mar. 15, 2016

(65) Prior Publication Data

US 2016/0194293 A1   Jul. 7, 2016

Related U.S. Application Data

(63) Continuation of application No. 12/513,341, filed as application No. PCT/EP2007/008732 on Oct. 9, 2007, now abandoned.

(30) Foreign Application Priority Data

Nov. 4, 2006  (EP) .................................... 06022990

(51) Int. Cl.
  *C07D 251/60*   (2006.01)
  *C07D 251/62*   (2006.01)
  *C07C 273/12*   (2006.01)
  *B01J 19/24*    (2006.01)
  *C07C 273/16*   (2006.01)

(52) U.S. Cl.
  CPC .......... *C07D 251/62* (2013.01); *B01J 19/245* (2013.01); *C07C 273/12* (2013.01); *C07C 273/16* (2013.01); *B01J 2219/24* (2013.01); *Y02P 20/125* (2015.11); *Y02P 20/582* (2015.11)

(58) Field of Classification Search
  CPC .... C07D 251/60; C07D 251/62; C07C 273/12

USPC .................................... 544/201, 203; 564/67
See application file for complete search history.

(56) References Cited

U.S. PATENT DOCUMENTS

| 3,239,522 A    | 3/1966  | Cook et al.     |
| 3,697,521 A    | 10/1972 | Van Nassau et al. |
| 6,114,579 A    | 9/2000  | Van Wijck       |
| 7,074,958 B2   | 7/2006  | Porro           |
| 7,414,130 B2   | 8/2008  | Brunengo et al. |
| 7,982,068 B2   | 7/2011  | Zardi et al.    |
| 2006/0052637 A1| 3/2006  | Porro           |
| 2007/0032650 A1| 2/2007  | Brunengo et al. |

FOREIGN PATENT DOCUMENTS

| CA | 838140 A     | 3/1970  |
| DE | 1468207 A1   | 11/1968 |
| DE | 2053358      | 5/1972  |
| GB | 1148767      | 4/1969  |
| GB | 1266363      | 3/1972  |
| WO | 98/08806 A1  | 3/1998  |
| WO | 02/090323 A1 | 11/2002 |
| WO | 2004/011419 A1 | 2/2004 |

OTHER PUBLICATIONS

Ulmann's Encyclopedia of Industrial Chemistry, Melamine and Guanamines, 2002, vol. 22, pp. 377-392.
Ripperger, "The World Melamine Industry", Nitrogen, No. 228, Jul.-Aug. 1997.
Gupta et al., "Emerging Trends in Ammonia and Urea Technology", Seminar Papers of FAI Seminar 2003 (Dec. 4-6, 2003, SII-3/1-16). http://onlinelibrary.wiley.com/doi/10.1002/14356007.a16_171.pub2/abstract.

*Primary Examiner* — Venkataraman Balasubramanian
(74) *Attorney, Agent, or Firm* — Akerman LLP (57) ABSTRACT

In an integrated process for urea and melamine production, urea is produced in a urea plant (10) comprising a high pressure urea synthesis section (11) from which an aqueous solution comprising urea, ammonium carbamate and ammonia is obtained and a urea recovery section (21) operating at low pressure, and melamine is produced in a melamine plant (40) wherein off-gases resulting as by-products of the melamine synthesis are discharged from said plant at a medium pressure and recycled to the high-pressure urea synthesis section (11).

11 Claims, 2 Drawing Sheets

INTEGRATED PROCESS FOR UREA AND MELAMINE PRODUCTION

CROSS-REFERENCE TO RELATED APPLICATIONS

This application is a continuation of U.S. patent application Ser. No. 12/513,341, filed May 1, 2009, which is a national phase of PCT/EP2007/008732, filed Oct. 9, 2007, and claims priority to European Patent Application No. 06022990.3, filed Nov. 4, 2006, the entire contents of which are incorporated herein by reference.

FIELD OF THE INVENTION

The present invention relates to a process for the integrated production of urea and melamine.

In particular, the present invention concerns a process of the above-identified type, wherein urea is produced in a urea plant comprising a high pressure urea synthesis section and a urea recovery section and wherein the off-gases resulting as by-products of the melamine synthesis are recycled to said high pressure urea synthesis section.

In the following description and subsequent claims, with the expression "high pressure urea synthesis section" it is intended to mean a section operated at a pressure of at least about 120 bar, generally between 130-260 bar.

More in particular, the process according to the present invention is of the type wherein the off-gases to be recycled have a pressure of at least 2 bar, generally between 2 and 30 bar.

The present invention is also concerned with an integrated plant for carrying out such a process.

As is known, in the field of urea and melamine there is increasingly felt the need of providing integrated processes wherein the off-gases produced in the melamine synthesis can be efficiently exploited for urea production.

PRIOR ART

In order to meet the above requirement, integrated processes have been proposed, wherein melamine is produced in a plant, so called melamine plant, using—as raw materials (reactants)—$NH_3$ and urea, the latter being produced in a plant for urea production, so called urea plant, to which the off-gases coming from the melamine plant and substantially containing $NH_3$ and $CO_2$, are recycled as raw materials (reactants).

According to these processes, the off-gases, generally discharged from the melamine plant at a pressure comprised between 2 and 30 bar, are appropriately treated before being fed into the urea plant.

In particular, the off-gases are condensed, at a pressure equal or lower than their discharge pressure, with a weak ammonia aqueous solution (ammonia concentration comprised between 0 to 15% by weight). The so obtained off-gas liquid solution is then fed to a waste water treatment section of the urea plant, generally operated at a pressure of about 2-5 bar, where $NH_3$ and $CO_2$ are recovered from the aqueous solution and recycled to the high pressure urea synthesis section, through the low pressure urea recovery section of the urea plant.

In the alternative, it has also been proposed to suitably compress the above off-gas liquid solution and recycle it directly to the high pressure synthesis section of the urea plant.

Although advantageous in some extent, the above processes are affected by several drawbacks.

In fact, in the first case, high energy consumption are required to separate $NH_3$ and $CO_2$ from the off-gas liquid solution in the waste water treatment section. Moreover, since the pressure in such a section is often much lower than the pressure of the off-gases discharged from the melamine plant, the off-gases have to be expanded before their condensation and recycle to the waste water treatment section of the urea plant, and thus there is also an energy waste in term of pressure loss.

In the second case, an additional, not negligible, amount of water is fed in the high pressure urea synthesis section through the recycled off-gas liquid solution. Since water is a by-product of the urea synthesis, its presence in the reactant feed is detrimental for the $CO_2$ conversion into urea. The urea conversion yield is thus negatively affected by the water contained in the recycled off-gas liquid solution with an ensuing increase in the energy consumption required for recovering urea from the urea solution leaving the synthesis section and for recycling the unconverted reagents back to the synthesis section.

In addition, such processes for the integrated production of urea and melamine are generally operated in connection with existing plants for the synthesis of urea and melamine, respectively, and they usually allow an increase, even significant, of the urea plant capacity compared with the design capacity for which such a plant had been designed. In order to face such capacity increases, the prior art provides for the substitution of undersized equipments, in particular the equipments of the high-pressure synthesis loop, with new equipments. It follows that the implementation of urea/melamine integrated processes of the prior art, in addition to the above mentioned drawbacks, is particularly burdensome from the economic, functional and energy consumption points of view.

SUMMARY OF INVENTION

The technical problem underlying the present invention is to provide an integrated process for urea and melamine production having functional features such as to fully overcome the drawbacks set forth with respect to the prior art and in which a higher production capacity for the urea plant can be achieved ensuring at the same time a high conversion yield of carbon dioxide to urea in a efficient way and with low energy consumption.

The above problem is solved, according to the invention, by an integrated process for urea and melamine production, wherein urea is produced in a urea plant comprising a high pressure urea synthesis section from which a aqueous solution comprising urea, ammonium carbamate and ammonia is obtained, and a low-pressure urea recovery section, and melamine is produced in a melamine plant wherein off-gases resulting as by-products of the melamine synthesis are discharged therefrom at a medium pressure and recycled to said high pressure urea synthesis section, the process being characterized in that it further comprises the steps of:

feeding at least a part of said aqueous solution comprising urea, ammonium carbamate and ammonia coming from said urea synthesis section to a medium-pressure treatment section of the urea plant for recovering ammonium carbamate and ammonia contained in it;

subjecting said part of aqueous solution comprising urea, ammonium carbamate and ammonia to dissociation in said medium-pressure treatment section, obtaining a urea aqueous solution and a vapour phase comprising ammonia, carbon dioxide and water;

feeding said urea aqueous solution obtained from dissociation in said treatment section to a decomposer of a urea recovery section operating at a predetermined low pressure, subjecting said urea aqueous solution to decomposition in said decomposer of said urea recovery section, obtaining a concentrated urea solution and a second vapour phase comprising ammonia, carbon dioxide and water;

subjecting said second vapour phase to condensation in a condenser of said urea recovery section in fluid communication with said decomposer, obtaining a recycle ammonium carbamate aqueous solution;

feeding said off-gases coming from said melamine plant and said recycle ammonium carbamate solution to a condensation section of said medium-pressure treatment section of the urea plant;

condensing said off-gases with said recycle carbamate aqueous solution in said condenser of the medium-pressure treatment section, obtaining a concentrated carbamate aqueous solution;

recycling said carbamate aqueous solution to said high pressure urea synthesis section.

Preferably, said medium-pressure treatment section of the urea plant operates to pressure substantially equal or lower than that of said off-gases discharged from said melamine plant.

In case the pressure of the recycle carbamate aqueous solution leaving the urea recovery section is lower than the operating pressure of the off-gas condensation section of the medium-pressure treatment section of the urea plant, then the process according to the present invention further comprises the step of compressing said recycle carbamate aqueous solution to a pressure substantially corresponding to the operating pressure of said off-gas condensation section, previous to feeding it in said condensation section.

The process of the invention further comprises the step of compressing said concentrated carbamate aqueous solution coming from said off-gas condensation section to a pressure substantially corresponding to the operating pressure of said high pressure urea synthesis section, previous to feeding (recycling) it to said urea synthesis section.

According to a preferred embodiment of the invention, said condensation section of the medium-pressure treatment section comprises a single condenser and the process further comprises the steps of:

feeding said vapour phase comprising ammonia, carbon dioxide and water, said off-gases and said recycle ammonium carbamate solution in said single condenser of the medium-pressure treatment section;

condensing said vapour phase comprising ammonia, carbon dioxide and water as well as said off-gases with said recycle ammonium carbamate solution in said single condenser of said medium-pressure treatment section, obtaining a concentrated ammonium carbamate aqueous solution; and recycling said concentrated ammonium carbamate aqueous solution to said high pressure urea synthesis section.

According to another embodiment of the invention, said condensation section of the medium-pressure treatment section comprises a first condenser and a second condenser in fluid communication to each other and the process further comprises the steps of feeding said off-gases coming from said melamine plant and said recycle ammonium carbamate solution to said first condenser of the medium-pressure treatment section of the urea plant;

condensing said off-gases with said recycle carbamate aqueous solution in said first condenser of the medium-pressure treatment section, obtaining a first concentrated ammonium carbamate aqueous solution;

feeding said first concentrated ammonium carbamate aqueous solution in said second condenser of the medium-pressure treatment section;

feeding said vapour phase comprising ammonia, carbon dioxide and water obtained from dissociation of said part of the aqueous solution comprising urea, ammonium carbamate and ammonia, in said second condenser of the medium-pressure treatment section;

condensing said vapour phase comprising ammonia, carbon dioxide and water with said first concentrated ammonium carbamate aqueous solution in said second condenser of the medium-pressure treatment section, obtaining a second concentrated ammonium carbamate aqueous solution; and recycling said second concentrated ammonium carbamate aqueous solution to said high pressure urea synthesis section.

Preferably, the process according to the invention further comprises the steps of:

feeding carbon dioxide to said condenser of said urea recovery section;

subjecting said carbon dioxide and said second vapour phase to condensation in said condenser of said urea recovery section, obtaining a recycle ammonium carbamato aqueous solution.

In this connection, particularly advantageous results have been obtained by feeding a carbon dioxide amount from 1 to 10 wt. % of the totality of feed carbon dioxide to said condenser of said urea recovery section.

Preferably, said part of aqueous solution comprising urea, ammonium carbamate and ammonia fed to said treatment section operating at medium pressure is comprised between 10 and 50 wt. % of said aqueous solution comprising urea, ammonium carbamate and ammonia obtained in said synthesis section.

Again preferably, said medium pressure of the treatment section is comprised between 10 and 70 bar.

Preferably, said off-gas condensation step with said recycle carbamate solution in said condensation section of the medium-pressure treatment section is of the double-effect type.

Thanks to the process according to the present invention, it has surprisingly and advantageously been found that the amount of condensation water (in absolute value) necessary to recycle the unreacted ammonia and the carbon dioxide in the form of ammonium carbamate to the synthesis section of the urea plant is substantially lower than the amount of condensation water (in absolute value) required to carry out such recycling with the processes according to the prior art, in which feed carbon dioxide and feed ammonia are fed to the medium pressure treatment section.

This is due to the fact that, with the same production capacity of the plant for urea production, the amount of ammonia and carbon dioxide to be recycled to the synthesis section in the form of ammonium carbamate is substantially less with the process according to the present invention with respect to with the processes of the prior art.

It follows that there is a significant increase in the conversion yield of the urea synthesis section, as well as of the overall yield of the H.P. Loop, to the great advantage of the efficiency and the energy consumption of the plant intended to carry out the process according to the present invention.

In addition, advantageously, the condensation of the off-gases is performed by exploiting the low amount of water already contained in the recycle carbamate aqueous solution obtained in the urea recovery section of the urea plant and which is anyway recycled to the high pressure urea synthesis section. Therefore, contrary to the processes of the prior art—no additional amount of water is added to the off-gasses when recycling them from the melamine plant to the urea plant. It follows that, thanks to the invention, a more concentrated carbamate solution is recycled to the high pressure urea synthesis section of the urea plant with the consequence that the urea conversion yield is advantageously increased and the energy consumption required for recovering urea and recycling the unconverted reagents to the synthesis section are advantageously substantially decreased.

According to a further aspect of the present invention, the present technical problem is solved by an integrated plant for implementing said process, wherein urea is produced in a urea plant comprising a high pressure urea synthesis section and a low pressure urea recovery section comprising a decomposer and a condenser, said section being in fluid communication to each other, and melamine is produced in a melamine plant wherein off-gases resulting as by-products of the melamine synthesis are discharged therefrom at a pressure of at least 2 bar and recycled to said high pressure urea synthesis section, the plant being characterized in that it further comprises:

a medium-pressure treatment section of the urea plant comprising a dissociator and a condensation section;

connecting means between said melamine synthesis section and said condensation section of the medium-pressure treatment section for feeding said off-gases coming from said melamine synthesis section to said condensation section of the medium-pressure treatment section;

connecting means between said condenser of the urea recovery section and said condensation section of the medium-pressure treatment section for feeding a recycle ammonium carbamate coming from said condenser of the urea recovery section to said condensation section of the medium-pressure treatment section; and connecting means between said dissociator of the medium-pressure treatment section and said decomposer of the low-pressure urea recovery section for feeding a urea aqueous solution obtained from dissociation in said treatment section to said decomposer of the urea recovery section.

According to an embodiment of the invention, said condensation section of the medium-pressure treatment section comprises a single condenser.

According to another embodiment of the invention, said condensation section of the medium-pressure treatment section comprises a first condenser and a second condenser and the integrated plant further comprises:

connecting means between said melamine synthesis section and said first condenser of the medium-pressure treatment section for feeding said off-gases coming from said melamine synthesis section to said first condenser of the medium-pressure treatment section;

connecting means between said condenser of the urea recovery section and said first condenser of the medium-pressure treatment section for feeding a recycle ammonium carbamate aqueous solution coming from said condenser of the urea recovery section to said first condenser of the medium-pressure treatment section;

connecting means between said first condenser and said second condenser of the medium-pressure treatment section for feeding a carbamate aqueous solution coming from said first condenser to said second condenser;

connecting means between said dissociator and said second condenser of the medium-pressure treatment section for feeding a vapour phase comprising ammonia, carbon dioxide and water from said dissociator to said second condenser of the medium-pressure treatment section.

Further characteristics and advantages of the process for the urea and melamine integrated production according to the invention will result from the following description of two preferred embodiments thereof given by way of non limiting example with reference to the attached drawings.

DETAILED DESCRIPTION OF A PREFERRED EMBODIMENT

Figure 1:
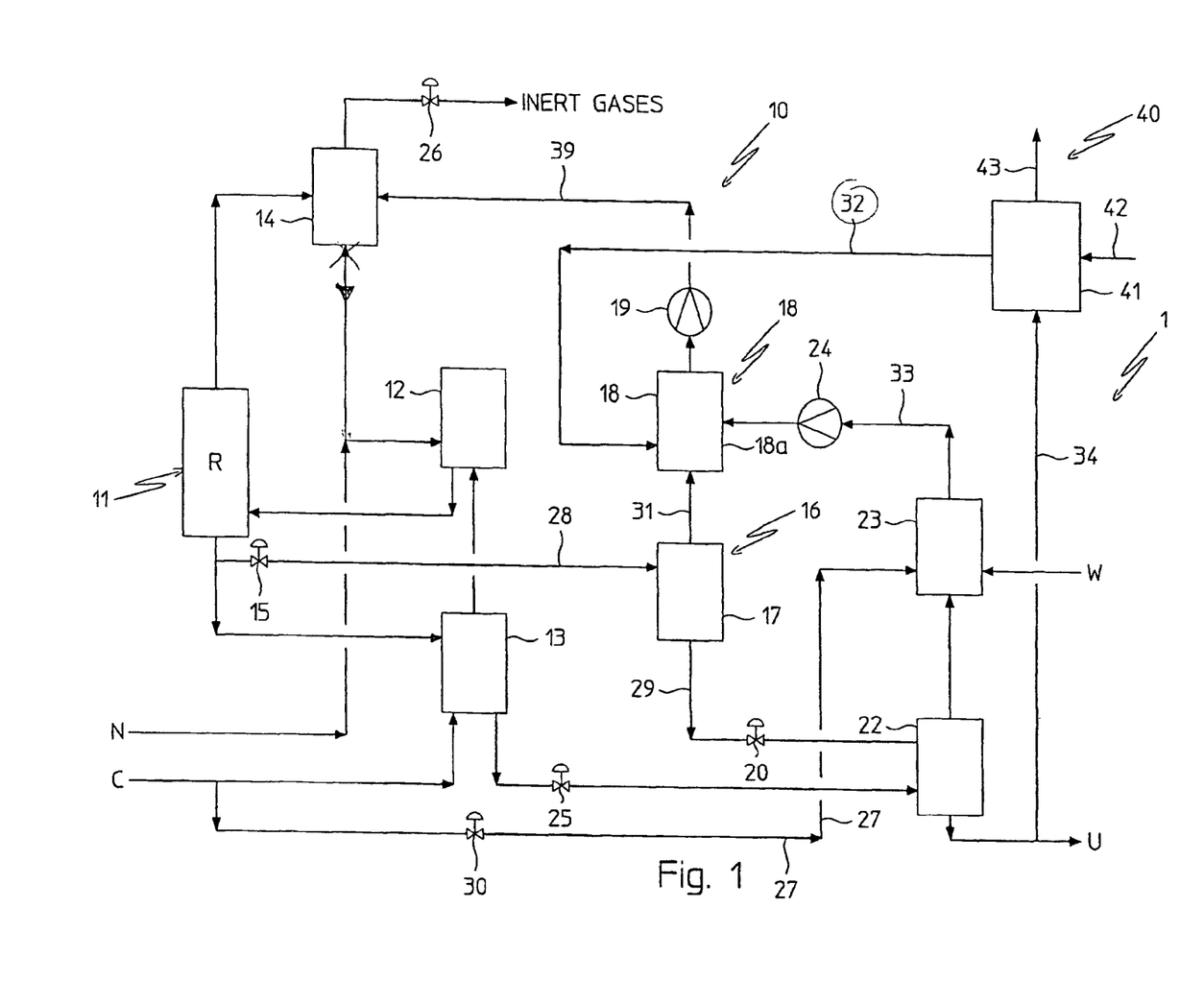
FIG. 1 schematically shows an integrated plant for urea and melamine production implementing the process according to an embodiment of the present invention.

With reference to FIG. 1, with number 1 is globally and schematically indicated an integrated plant for urea and melamine production according to the present invention. The integrated plant 1 comprises a plant 40 for the production of melamine and a plant 10 for the production of urea The melamine plant 40 of the present invention can be of the catalytic low pressure type (up to 70 bar) or of the non-catalytic high pressure type (above 70 bar), provided that the off-gases discharged from the melamine plant have a pressure of at least 10 bar (medium pressure). The plant 40 comprises a low pressure or high pressure melamine synthesis section, globally indicated with number 41.

Preferably, but non exclusively, the melamine plant 40 is of the non-catalytic high pressure type, wherein the off-gases discharged as by-products of the melamine synthesis have a pressure comprised between 10 and 70 bar, preferably between 20 and 30 bar, for example 25 bar. Of course, the off-gasses discharged from the melamine plant according to the present invention can also have a much higher pressure, depending on the pressure at which melamine is produced.

The urea plant 10 of the present invention is of the total recycle type, and comprises—according to a first aspect of the present invention—a synthesis section 11 operating at a predetermined high pressure (at least 120 bar, generally at about 130-260 bar), a treatment section 16 operating at medium pressure (preferably 10-70 bar) and a urea recovery section 21 operating at a predetermined low pressure (about 2-10 bar), said sections 11, 16 and 21 being in fluid communication to each other.

In the integrated process according to the invention, ammonia N and carbon dioxide C for urea production are fed into an appropriate synthesis section 11. In the example of FIG. 1, the urea synthesis section comprises a single reactor R.

In particular, according to such an example, the ammonia N is fed to the reactor R through a condenser 12 and the carbon dioxide C is in turn fed to the reactor R through a stripper 13 and the condenser 12.

The synthesis section 11 (reactor R), the condenser 12, the stripper 13, together with a scrubber 14 (that shall be described hereafter in greater detail), all operate substantially at the same high pressure, thus constituting the high pressure synthesis loop (H.P. Loop) of the process of the present invention.

In the reactor R, or rather in the synthesis section 11, the ammonia and carbon dioxide are made to react at the aforementioned predetermined high pressure (for example comprised between 130 and 170 bar) and at a predetermined high temperature (for example comprised between 160 and 200° C.). From the reactor R an aqueous solution comprising urea, ammonium carbamate and ammonia is obtained.

A part of the aqueous solution comprising urea, ammonium carbamate and ammonia exiting the reactor R is suitably decompressed in a per se conventional way for example by means of a valve 15 and fed to a treatment section 16 of such an aqueous solution operating at a predetermined medium pressure, for example comprised between 10 and 70 bar, preferably comprised between 15 and 30 bar, and even more preferably comprised between 18-20 bar.

For the recovery of the ammonium carbamate and of the ammonia, the part of aqueous solution comprising urea, ammonium carbamate and ammonia suitably decompressed is fed to a medium pressure dissociator 17 at the treatment section 16 and subjected to dissociation obtaining an urea aqueous solution and a vapour phase comprising ammonia, carbon dioxide and water. In particular, such a part of aqueous solution comprising urea, ammonium carbamate and ammonia is subjected in the dissociator 17 to thermal dissociation.

The vapour phase comprising ammonia, carbon dioxide and water thus obtained is then fed and subjected to condensation in a medium pressure condenser 18 of the treatment section 16 in the way that will be explained later.

In the example of FIG. 1, the condensation unit 18 of the medium-pressure treatment section 16 comprises a single condenser 18a.

According to a further aspect of the present invention, the integrated process for urea and melamine production advantageously provides for the step of feeding the urea aqueous solution obtained by dissociation in the medium pressure dissociator 17 of the treatment section 16 to a decomposer 22 of a urea recovery section 21 operating at a predetermined low pressure, for example comprised between 1.5 and 9.5 bar, preferably comprised between 3 and 5 bar.

For this purpose, the urea aqueous solution exiting the dissociator 17 is suitably decompressed in a per se conventional way for example by means of a valve 20.

In particular, as represented in the preferred embodiment of the process according to the present invention of FIG. 1, the urea aqueous solution exiting the dissociator 17 of the treatment section 16 is directly fed to the decomposer 22 of the urea recovery section 21.

Moreover, again in accordance with the example of FIG. 1, a part of the feed carbon dioxide C is preferably and advantageously fed to a condenser 23 of the low pressure urea recovery section 21.

For this purpose, such a part of feed carbon dioxide C sent to the condenser 23 is suitably decompressed in a per se conventional way for example by means of a valve 30.

In the decomposer 22 of the low pressure urea recovery section 21, the urea aqueous solution coming from the dissociator 17 of the medium pressure treatment section 16 is subjected to decomposition, obtaining a concentrated urea solution U and a second vapour phase comprising ammonia, carbon dioxide and water.

Advantageously, the concentrated urea solution U, for example with a urea concentration comprised between 60 and 80 wt. %, exits the decomposer 22 of the urea recovery section 21 and it is used at least in part as reactant in the melamine plant 40.

As an alternative, urea is fed into the melamine synthesis section 41 in form of molten urea coming from the final urea treatment section (not shown) provided downstream the urea recovery section 16.

To this aim, the concentrated urea solution, or a portion thereof, is fed, through flow line 34, to the melamine synthesis section 41. In the example of FIG. 1, not all the urea produced in the plant 10 is used for the melamine synthesis and thus a portion of the concentrated urea solution is subjected to the final urea treatment steps (per se conventional and then not shown) of the process for urea production, such as the steps of decomposition under vacuum and granulation or prilling of the molten urea so obtained.

To control the melamine synthesis, section 41 can optionally also be fed with an additional flow of ammonia, indicated in FIG. 1 by flow line 42.

From the melamine synthesis section 41, a melamine solution is discharged, through flow line 43, for further processing such as cooling (not shown), where melamine is converted into a powder and exits the integrated plant 1.

Instead the off-gases consisting essentially of carbon dioxide and ammonia that are also obtained in section 41, as by-products of the melamine synthesis, leaves said section 41 through flow line 32. Generally, before leaving the melamine synthesis section 41, the off-gases are suitably washed (scrubbed), not shown, with the feed concentrated urea solution in order to remove possible liquid melamine entrained in such gases.

In accordance with another aspect of the integrated process according to the present invention, the second vapour phase comprising ammonia, carbon dioxide and water obtained in the decomposer 22 of the urea recovery section 21 is sent to the condenser 23 of the same section 21 and advantageously subjected to condensation, obtaining a recycle carbamate aqueous solution.

Preferably, as represented in the example of FIG. 1, the second vapour phase comprising ammonia, carbon dioxide and water is subjected to condensation together with the feed carbon dioxide C fed to said condenser 23.

A suitable amount of a carbamate aqueous solution W (carbonate) having a condensation water content comprised between 30 and 80 wt. % is also fed to the condenser 23 of the low pressure urea recovery section 21, to allow the second vapour phase and the feed carbon dioxide C, respectively, to condense to ammonium carbamate.

The carbamate aqueous solution W (carbonate) generally comes from a treatment section of the process condensate and/or from an ammonia liquor reservoir, per se conventional and not represented in FIG. 1.

In accordance with the present invention, as represented in the example of FIG. 1, the recycle carbamate aqueous solution obtained in the condenser 23 of the low pressure urea recovery section 21 is, according to the present process, fed to the condenser 18a of the medium pressure treatment section 16 for the condensation of the vapour phase comprising ammonia, carbon dioxide and water coming from the medium pressure dissociator 17 as well as of the off-gases discharged from the melamine synthesis section 41 of the melamine plant 40.

To this purpose, said off-gases are fed to the condenser 18a of the medium-pressure section 16 through said flow line 32 while said vapour phase coming from the dissociator 17 and said recycle carbamate solution are fed to said condenser 18 through flow lines 31 and 33 respectively.

Preferably, the condenser 18a of the medium-pressure section 16 is operated substantially at the same pressure as that of the off-gases discharged form the melamine synthesis section 41.

In the case the pressure of the off-gases coming from the melamine synthesis section 41 is higher than the pressure of the recycle carbamate aqueous solution discharged from the urea recovery section 16, the latter solution, as shown in FIG. 1, is advantageously compressed, through a first compression section 24, to the pressure of such off-gases i.e. to the operating pressure of the condenser 18 of the medium-pressure treatment section 16.

According to an alternative embodiment of the process of the present invention, not shown, the condensation step in the condenser 18a of the medium-pressure treatment section 16 is of the double-effect type, in which the condensation heat, instead of being dissipated in a cooling fluid (generally cooling water), is advantageously exploited for further concentrating the concentrated urea solution U exiting the decomposer 22 of the low-pressure urea recovery section.

In this case, the condensation heat produced during condensation of the vapour phase is transmitted to the concentrated urea solution by indirect thermal exchange, allowing the decomposition and then the separation of the part of the ammonium carbamate, ammonia and water still present in said solution and then further concentrating urea contained into it.

In the example of FIG. 1, the concentrated carbamate aqueous solution exiting the medium-pressure condenser 18a is duly compressed in a second compression section 19, in a per se convantial way, and is recycled to the reactor R of the high-pressure urea synthesis section 11 through the scrubber 14 and the high-pressure condenser 12.

According to an alternative embodiment of the present invention, not shown, at least of a part of the carbamate aqueous solution exiting the medium-pressure condenser 18a is fed directly, duly compressed, to the high-pressure condenser 12 and it then flows to the reactor R.

The remaining part of aqueous solution comprising urea, ammonium carbamate and ammonia, exiting the reactor R and not sent to the medium pressure treatment section 16, is subjected to the recovery phase of the ammonium carbamate and of the ammonia present in such a solution, in the high pressure loop of the present process.

In particular, the remaining part of the aqueous solution comprising urea, ammonium carbamate and ammonia exiting the reactor R of the synthesis section 11 is fed to the high pressure stripper 13 where it is subjected to decomposition and stripping with feed carbon dioxide C. The ammonia and carbon dioxide thus produced are then recondensed (partially) into ammonium carbamate in the high pressure condenser 12 and recycled in the form of ammonium carbamate to the reactor R of the urea synthesis section 11.

The condensation in the high pressure condenser 12 of the ammonia and carbon dioxide coming from the stripper 13 is made to occur by absorption of such gases with the feed ammonia N (liquid) and with the carbamate aqueous solution coming, suitably compressed, from the condenser 18 of the medium pressure treatment section 16, through the scrubber 14.

The aqueous solution comprising urea, ammonium carbamate and ammonia obtained in the stripper 13, following the aforementioned decomposition and stripping steps with $CO_2$, is suitably decompressed in a per se conventional way for example by means of a valve 25 at the operating pressure of the urea recovery section 21 and fed to the low pressure decomposer 22 of such a section 21. Here, such a solution is subjected to decomposition, together with said urea aqueous solution coming from the dissociator 17 of the medium pressure treatment section 16, obtaining the concentrated urea solution U and the second vapour phase comprising ammonia, carbon dioxide and water, described above.

The unreacted carbon dioxide and ammonia and water in vapour phase present in the urea synthesis section 11, or rather in the reactor R, are made to exit the latter and fed to the high pressure scrubber 14. These vapours generally also comprise inert gases (for example air) present in the feed carbon dioxide C.

In the scrubber 14, the aforementioned vapours are subjected to a washing treatment with the carbamate aqueous solution coming, suitably compressed, from the condenser 18a of the medium pressure treatment section 16, for the recovery of the carbon dioxide and ammonia present in them and the separation of the inert gases. The inert gases thus separated are then released into the atmosphere in a per se conventional manner, moreover providing suitable decompression thereof for example by means of a valve 26. Alternatively, such inert gases can be recycled in other parts of the plant 10 (not represented). The carbon dioxide and ammonia absorbed in the carbamate aqueous solution coming from the condenser 18 are, on the other hand, recycled to the urea synthesis section 11, or rather to the reactor R, through the high pressure condenser 12.

Figure 2:
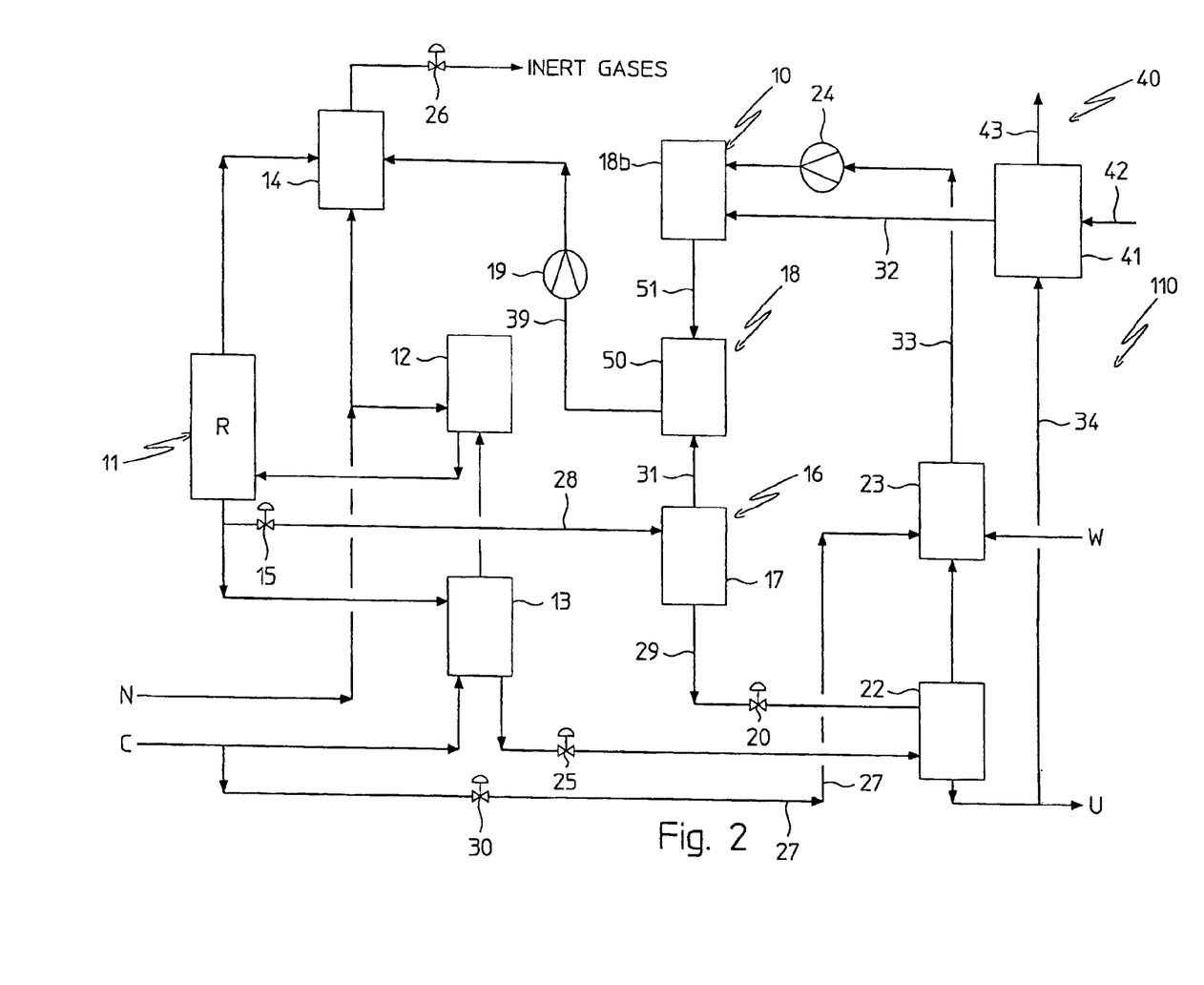
FIG. 2 schematically shows an integrated plant for urea and melamine production implementing the process according to another embodiment of the present invention.

In FIG. 2, with number 110 is globally and schematically indicated an integrated plant for urea and melamine production according to another embodiment of the present invention.

In the integrated plant 110, elements which are structurally or functionally equivalent to corresponding elements of the integrated plant 1 described above will be given the same reference numerals and, for sake of brevity, will not be further described.

The integrated plant 110 differs from the plant 1 described above in that the condensation unit 18 of the medium-pressure treatment section 16 of the urea plant 10 comprises a first condenser 18b and second condenser 50 in fluid communication to each other, instead of a single condenser.

In addition, in the first condenser 18b of the medium-pressure treatment section 16 are fed the off-gases coming from the synthesis section 41 of the melamine plant, through the flow line 32 and the recycle carbamate solution coming from the condenser 23 of the urea recovery section 21, through the flow line 33, while the vapour phase coming from the dissociator 17 is fed, through the flow line 31, to the second condenser 50 of the medium-pressure treatment section 16.

In the second condenser 50, said vapour phase is condensed through said concentrated carbamate aqueous solution obtained from the condensation of the off-gases in the first condenser 18b, which concentrated carbamate solution is fed to the second condenser through the flow line 51.

A more concentrated carbamate solution is then obtained at the exit of the second condenser 50 which is recycled to the urea synthesis section 11 in the way indicated above with reference to the integrated plant 1.

Preferably, in the integrated plant 110, the condensation step in the condenser 18b of the medium-pressure treatment section 16 is of the double-effect type, in which the condensation heat, instead of being dissipated in a cooling fluid (generally cooling water), is advantageously exploited for further concentrating the concentrated urea solution U exiting the decomposer 22 of the low-pressure urea recovery section.

In the integrated plants described above, the flow lines indicated in FIGS. 1 and 2 with references 27-29, 31-34, 39, 42, 43 and 51 represent schematically per se conventional conduits and/or ducts.

With the process according to the invention, particularly advantageous results have been obtained by feeding an amount of feed carbon dioxide C comprised between 1 and 5 wt. %, even more preferably comprised between 2 and 3 wt. %, of all of the feed carbon dioxide C fed to the plant 10, to the condenser 23 of the low pressure urea recovery section 21.

Moreover, the part of aqueous solution comprising urea, ammonium carbamate and ammonia sent to the medium pressure treatment section 16 is preferably comprised between 10 and 50 wt. %, even more preferably comprised between 10 and 25 wt. %, of the aqueous solution coming from the urea synthesis section 11.

With reference to FIGS. 1 and 2, the structural features of the plants 1 and 110 for the integrated urea and melamine production according to the process of the present invention just described shall now be better specified.

In accordance with the present invention, the integrated plants 1 and 110 comprise each a urea plant 10 comprising a high pressure urea synthesis section 11, a medium-pressure treatment section 16 for a part of the urea solution produced in said synthesis section 11, comprising a dissociator 17 and a condensation unit 18, and a low pressure urea recovery section 21 comprising a decomposer 22 and a condenser 23, said sections 11, 16 and 21 being in fluid communication to each other, and a melamine plant 40 comprising a melamine synthesis section 41 wherein off-gases resulting as by-products of the melamine synthesis are discharged from said plant 40 at a pressure of at least 2 bar and recycled to said high pressure urea synthesis section.

The plants 1 and 110 further comprise:
connecting means 32 between said melamine synthesis section 41 and said condensation section 18 of the medium-pressure treatment section for feeding said off-gases coming from said melamine synthesis section 41 to said condensation section 18 of the medium-pressure treatment section 16;
connecting means 33 between said condenser 23 of the urea recovery section 21 and said condensation section 18 of the medium-pressure treatment section 16 for feeding a recycle ammonium carbamate coming from said condenser 23 of the urea recovery section 21 to said condensation section 18 of the medium-pressure treatment section 16; and
connecting means 29 between said dissociator 17 of the medium-pressure treatment section and said decomposer 22 of the low-pressure urea recovery section 21 for feeding a urea aqueous solution obtained from dissociation in said treatment section 16 to said decomposer 22 of the urea recovery section.

According to an embodiment of the invention, said condensation section of the medium-pressure treatment section comprises a single condenser.

The plants 1 and 110 further comprise connecting means 31 between said dissociator 17 and said condensation unit 18 of the medium-pressure treatment section 16 for feeding a vapour phase comprising ammonia, carbon dioxide and water from said dissociator 17 to said condenser 18 of the medium-pressure treatment section.

In the plants 1 and 110, said connecting means essentially consists of per se conventional conduits and/or ducts.

The plants 1 and 110 further comprise a first compressing section 24 located, in fluid communication, between the condenser 23 of the urea recovery section 21 and the condensation unit 18 of the medium-pressure treatment section 16 for compressing a recycle carbamate solution coming from said condenser 23 of the urea recovery section 21 to a pressure corresponding to the operative pressure of said condensation unit 18 of the medium-pressure treatment section 16, as well as a second compressing section 19 located, in fluid communication, between said condensation unit 18 of the medium-pressure treatment section 16 and said high-pressure urea synthesis section 11 for compressing a concentrated carbamate solution coming from said condensation unit 18 of the medium-pressure treatment section 16 to a pressure corresponding to the operative pressure of said high-pressure urea synthesis section 11.

In the plants 1 and 110, said first compressing section 24 and said second compression section 19 comprise at least a per se conventional pump.

According to an embodiment of the invention (integrated plant 1 of FIG. 1), the condensation unit 18 of the medium-pressure treatment section 16 comprises a single condenser 18a.

According to another embodiment of the invention (integrated plant 110 of FIG. 2) the condensation unit 18 of the medium-pressure treatment section 16 comprises a first condenser 18b and a second condenser 50. In addition, the integrated plant 110 comprises:
connecting means 32 between said melamine synthesis section 41 and said first condenser 18b of the medium-pressure treatment section 16 for feeding said off-gases coming from said melamine synthesis section 41 to said first condenser 18b of the medium-pressure treatment section 16;
connecting means 33 between said condenser 23 of the urea recovery section 21 and said first condenser 18b of the medium-pressure treatment section for feeding a recycle ammonium carbamate aqueous solution coming from said condenser 23 of the urea recovery section 21 to said first condenser 18b of the medium-pressure treatment section 16;
connecting means 51 between said first condenser 18b and said second condenser 50 of the medium-pressure treatment section 16 for feeding a carbamate aqueous solution coming from said first condenser 18b to said second condenser 50; and
connecting means between said dissociator 17 and said second condenser 50 of the medium-pressure treatment section 16 for feeding a vapour phase comprising ammonia, carbon dioxide and water from said dissociator 17 to said second condenser 50 of the medium-pressure treatment section.

Furthermore, according to the invention, the integrated plants 1 and 110 comprise connecting means 39 between said single condenser 18 or said second condenser 50 of the medium-pressure treatment section 16 and said urea synthesis section 11 for feeding a carbamate solution coming from said single condenser 18 or said second condenser 50 in said urea synthesis section 11, as well as connecting means 27 for feeding feed carbon dioxide C to said condenser 23 of the low-pressure urea recovery section 21.

Preferably, in the plant 1 of FIG. 1, the single condenser 18a of the medium-pressure treatment section 16 comprises a conventional tube bundle, in fluid communication, on the tube side, with the concentrated urea solution U exiting the low pressure decomposer 22 of the low-pressure urea recovery section 21 and, on the shell side, with the vapour phase comprising ammonia, carbon dioxide and water coming from the dissociator 17 of the medium-pressure treatment section 16, with off-gases coming from the melamine synthesis section 41 as well as with the recycle carbamate aqueous solution coming from the condenser 23 of the low-pressure urea recovery section 21.

Preferably, in the plant 110 of FIG. 2, the first condenser 18b of the medium-pressure treatment section 16 comprises a conventional tube bundle, in fluid communication, on the tube side, with the concentrated urea solution U exiting the low pressure decomposer 22 of the low-pressure urea recovery section 21 and, on the shell side, with off-gases coming from the melamine synthesis section 41 as well as with the recycle carbamate aqueous solution coming from the condenser 23 of the low-pressure urea recovery section 21.

From the previous description it can clearly be seen that the integrated process for urea and melamine production according to the invention solves the technical problem and achieves numerous advantages the first of which lies in the fact that a high overall conversion yield is obtained in the high pressure loop, and in particular in the urea synthesis section, for example comprised between 58 and 62 wt. %, even in the case of revamping pre-existing high-capacity integrated plants in which for example the urea plant can produce between 3000 and 4500 Metric Ton/day of urea.

A further advantage lies in that the more concentrated carbamate aqueous solution can be recycled to the synthesis section of the urea plant, obtaining advantageously a higher urea conversion yield and a reduction of energy consumption since the condensation of off-gases is performed by exploiting the low amount of water already contained in the recycle carbamate aqueous solution obtained in the urea recovery section of the urea plant which is anyway recycled to the high-pressure synthesis section of the urea plant.

A further advantage is that, thanks to the present invention and in particular to the high conversion yield, it is possible to reduce the energy consumption of the high pressure synthesis loop as well as of the low pressure urea recovery section, with respect to the processes according to the prior art. It follows from this that with the same energy consumption and size of the apparatuses that constitute the plant for urea production, the process according to the present invention allows operation in such a plant with a higher production capacity with respect to what is allowed with the processes according to the prior art. In other words, with the same production capacity, the plant intended to carry out the process according to the present invention is smaller in size, and thus more cost-effective and with less operating costs, with respect to the plant necessary to obtain such a capacity with the methods of the prior art.

Moreover, the actuation of the process is particularly simple and reliable, and does not require large investment costs.

Among the numerous advantages achieved by the present invention, it is worth to cite also the possibility of revamping pre-existing plants for the urea and melamine integrated production, for the purpose of increasing the production capacity and the production yield of the urea plant as well as of reducing the relative energy consumption with the process according to the invention.

Of course, a man skilled in the art may contribute numerous modifications and changes to the process for the urea and melamine integrated production described above for satisfying specific and contingent requirements, all falling within the scope of protection of the invention itself, as it is defined by the following claims.

The invention claimed is:

1. An integrated process for urea and melamine production, wherein urea is produced in a urea plant comprising a high-pressure urea synthesis loop comprising a high pressure urea synthesis section from which a aqueous solution comprising urea, ammonium carbamate and ammonia is obtained, a high pressure condenser and a high pressure stripper, and a low-pressure urea recovery section, and melamine is produced in a melamine plant wherein off-gases resulting as by-products of the melamine synthesis are discharged therefrom at a medium pressure and recycled to said high pressure urea synthesis section, comprising the steps of:
    feeding a part of said aqueous solution comprising urea, ammonium carbamate and ammonia coming from said urea synthesis section to a medium-pressure treatment section of the urea plant for recovering ammonium carbamate and ammonia contained in it;
    subjecting said part of aqueous solution comprising urea, ammonium carbamate and ammonia to dissociation in said medium-pressure treatment section, obtaining a first urea aqueous solution and a first vapour phase comprising ammonia, carbon dioxide and water;
    feeding said first urea aqueous solution obtained from dissociation in said treatment section to a decomposer of a urea recovery section operating at a predetermined low pressure,
    feeding a remaining part of said aqueous solution comprising urea, ammonium carbamate and ammonia coming from said urea synthesis section to said high pressure stripper;
    subjecting said remaining part of aqueous solution comprising urea, ammonium carbamate and ammonia to decomposition and stripping in said high pressure stripper, obtaining a second urea aqueous solution and a second vapour phase comprising ammonia and carbon dioxide;
    feeding said second urea aqueous solution obtained from decomposition and stripping in said high pressure stripper to said decomposer of said urea recovery section,
    subjecting said first and second urea aqueous solution to decomposition in said decomposer of said urea recovery section, obtaining a concentrated urea solution and a third vapour phase comprising ammonia, carbon dioxide and water;
    subjecting said third vapour phase to condensation in a condenser of said urea recovery section in fluid communication with said decomposer, obtaining a recycle ammonium carbamate aqueous solution;
    feeding said off-gases coming from said melamine plant and said recycle ammonium carbamate solution to a condensation section of said medium-pressure treatment section of the urea plant;
    condensing said off-gases with said recycle carbamate aqueous solution in said condensation unit of the medium-pressure treatment section, obtaining a concentrated carbamate aqueous solution; and
    recycling said carbamate aqueous solution to said high pressure urea synthesis section.

2. The process according to claim 1, wherein said medium-pressure treatment section of the urea plant operates to pressure substantially equal or lower than that of said off-gases.

3. The process according to claim 1, wherein said recycle carbamate solution coming from the urea recovery section is fed directly to said medium-pressure treatment section for condensing said off-gases.

4. The process according to claim 1, wherein said recycle carbamate solution coming from the urea recovery section is compressed to a pressure substantially corresponding to the operating pressure of said medium-pressure treatment section for condensing said off-gases, before feeding it into said condensation unit.

5. The process according to claim 1, wherein said concentrated carbamate aqueous solution coming from said condensation unit of the medium-pressure treatment section is compressed to a pressure substantially corresponding to the operating pressure of said urea synthesis section, before feeding it to said urea synthesis section.

6. The process according to claim 1, wherein said condensation unit of the medium-pressure treatment section comprises a single condenser and in that the process further comprises the steps of:
- feeding said vapour phase comprising ammonia, carbon dioxide and water, said off-gases and said recycle ammonium carbamate solution in said single condenser of the medium-pressure treatment section;
- condensing said vapour phase comprising ammonia, carbon dioxide and water as well as said off-gases with said recycle ammonium carbamate solution in said single condenser of said medium-pressure treatment section, obtaining a concentrated ammonium carbamate aqueous solution; and
- recycling said concentrated ammonium carbamate aqueous solution to said high pressure urea synthesis section.

7. The process according to claim 1, wherein said condensation unit of the medium-pressure treatment section comprises a first condenser and a second condenser in fluid communication to each other and in that the process further comprises the steps of:
- feeding said off-gases coming from said melamine plant and said recycle ammonium carbamate solution to said first condenser of the medium-pressure treatment section of the urea plant;
- condensing said off-gases with said recycle carbamate aqueous solution in said first condenser of the medium-pressure treatment section, obtaining a first concentrated ammonium carbamate aqueous solution;
- feeding said first concentrated ammonium carbamate aqueous solution in said second condenser of the medium-pressure treatment section;
- feeding said vapour phase comprising ammonia, carbon dioxide and water obtained from dissociation of said part of the aqueous solution comprising urea, ammonium carbamate and ammonia, in said second condenser of the medium-pressure treatment section; and
- condensing said vapour phase comprising ammonia, carbon dioxide and water with said first concentrated ammonium carbamate aqueous solution in said second condenser of the medium-pressure treatment section, obtaining a second concentrated ammonium carbamate aqueous solution; and
- recycling said second concentrated ammonium carbamate aqueous solution to said high pressure urea synthesis section.

8. The process according to claim 1, wherein it comprises the further steps of:
- feeding carbon dioxide to said condenser of said urea recovery section; and
- subjecting said carbon dioxide and said second vapour phase to condensation in said condenser of said urea recovery section, obtaining a recycle ammonium carbamate aqueous solution.

9. The process according to claim 8, characterized by feeding a carbon dioxide amount from 1 to 10 wt. % of the totality of feed carbon dioxide to said condenser of said urea recovery section.

10. The process according to claim 1, wherein said part of aqueous solution comprising urea, ammonium carbamate and ammonia fed to said treatment section operating at medium pressure is comprised between 10 and 50 wt. % of said aqueous solution comprising urea, ammonium carbamate and ammonia obtained in said synthesis section.

11. The process according to claim 1, wherein said medium pressure of the treatment section is comprised between 10 and 70 bar.

* * * * *